(12) United States Patent
Lindeburg

(10) Patent No.: US 11,337,849 B2
(45) Date of Patent: May 24, 2022

(54) OCCLUSION DEVICE FOR REVERSIBLE OCCLUSION OF A BIOLOGICAL TUBE

(71) Applicant: VasDeBlock ApS, Karise (DK)

(72) Inventor: Niels Lindeburg, Karise (DK)

(73) Assignee: VasDeBlock ApS, Karise (DK)

( * ) Notice: Subject to any disclaimer, the term of this patent is extended or adjusted under 35 U.S.C. 154(b) by 376 days.

(21) Appl. No.: 15/573,359

(22) PCT Filed: May 12, 2016

(86) PCT No.: PCT/DK2016/050129
§ 371 (c)(1),
(2) Date: Nov. 10, 2017

(87) PCT Pub. No.: WO2016/180426
PCT Pub. Date: Nov. 17, 2016

(65) Prior Publication Data
US 2018/0133049 A1    May 17, 2018

(30) Foreign Application Priority Data

May 12, 2015   (EP) .................................... 15167312

(51) Int. Cl.
*A61F 6/22* (2006.01)
*A61F 6/20* (2006.01)
(Continued)

(52) U.S. Cl.
CPC ............ *A61F 6/22* (2013.01); *A61B 17/1204* (2013.01); *A61B 17/12136* (2013.01);
(Continued)

(58) Field of Classification Search
CPC ........... A61B 17/1204; A61B 17/12136; A61F 6/146; A61F 6/225; A61F 6/06; A61F 6/24; A61M 25/1011
(Continued)

(56) References Cited

U.S. PATENT DOCUMENTS

| 3,648,683 A | 3/1972 | Brodie |
| 4,052,754 A | 10/1977 | Homsy |

(Continued)

FOREIGN PATENT DOCUMENTS

| EP | 2 404 580 A1 | 1/2012 | |
| EP | 2404580 A1 * | 1/2012 | ............. A61F 6/005 |

OTHER PUBLICATIONS

Luca Carmignani, Emanuele Montanari, Franco Gadda, Giorgio Bozzini, Francesco Rocco, and Giovanni Maria Colpi, Dec. 2005, Journal of Endourology, vol. 19, Issue 10. Abstract. (Year: 2005).*

*Primary Examiner* — Keri J Nelson
*Assistant Examiner* — Trisha Talapatra
(74) *Attorney, Agent, or Firm* — Holland & Hart LLP

(57) ABSTRACT

The present methods, systems, and devices relate to an occlusion device for blocking a biological tube, the biological tube being prone to a peristaltic wave having a wave length, and where the occlusion device comprises at least two sections, where each section is connected by at least one narrowing to at least one other section. The occlusion device is of an elastic material, and each section is configured to deform when a force is applied by the peristaltic wave, and the length of at least one of the at least two sections corresponds substantially to the wave length of the peristaltic wave in the biological tube, so as to absorb the peristaltic wave. The methods, systems, and devices relates to reversible contraception of female and/or male gendered species intervening with biological tube, which are responsible for transportation of fertility fluids, such as the transportation of spermatozoes or oocytes in for example the human reproductive system.

13 Claims, 7 Drawing Sheets

(51) Int. Cl.
   *A61B 17/12*   (2006.01)
   *A61B 17/00*   (2006.01)
(52) U.S. Cl.
   CPC ......... *A61B 17/12163* (2013.01); *A61F 6/20* (2013.01); *A61B 2017/00858* (2013.01); *A61B 2017/00862* (2013.01); *A61B 2017/00951* (2013.01)
(58) Field of Classification Search
   USPC ......... 606/197–198; 128/831, 836, 838, 840, 128/843, 887; 604/9
   See application file for complete search history.

(56) References Cited

U.S. PATENT DOCUMENTS

| | | | | |
|---|---|---|---|---|
| 4,682,592 | A * | 7/1987 | Thorsgard | A61F 6/202 |
| | | | | 128/843 |
| 5,954,715 | A * | 9/1999 | Harrington | A61B 18/1485 |
| | | | | 606/28 |
| 8,100,129 | B2 * | 1/2012 | Swann | A61B 8/481 |
| | | | | 128/831 |
| 2003/0066533 | A1 | 4/2003 | Loy | |
| 2005/0192616 | A1 * | 9/2005 | Callister | A61B 17/12022 |
| | | | | 606/193 |
| 2009/0078270 | A1 * | 3/2009 | Meier | A61F 6/20 |
| | | | | 128/843 |
| 2010/0063531 | A1 * | 3/2010 | Rudakov | A61B 17/12022 |
| | | | | 606/194 |
| 2010/0192959 | A1 * | 8/2010 | Shandas | A61L 31/048 |
| | | | | 128/831 |
| 2013/0110081 | A1 * | 5/2013 | Roorda | A61B 17/12022 |
| | | | | 604/509 |
| 2015/0105816 | A1 * | 4/2015 | Rasmusson | A61M 25/1011 |
| | | | | 606/194 |
| 2016/0089255 | A1 * | 3/2016 | Bergheim | A61B 17/12145 |
| | | | | 604/9 |
| 2017/0136143 | A1 * | 5/2017 | Herr | A61B 8/0833 |
| 2017/0360550 | A1 * | 12/2017 | Foote | A61F 2/04 |
| 2018/0368965 | A1 * | 12/2018 | Janardhan | A61B 17/22 |
| 2019/0282270 | A1 * | 9/2019 | Lee-Sepsick | A61F 2/954 |

* cited by examiner

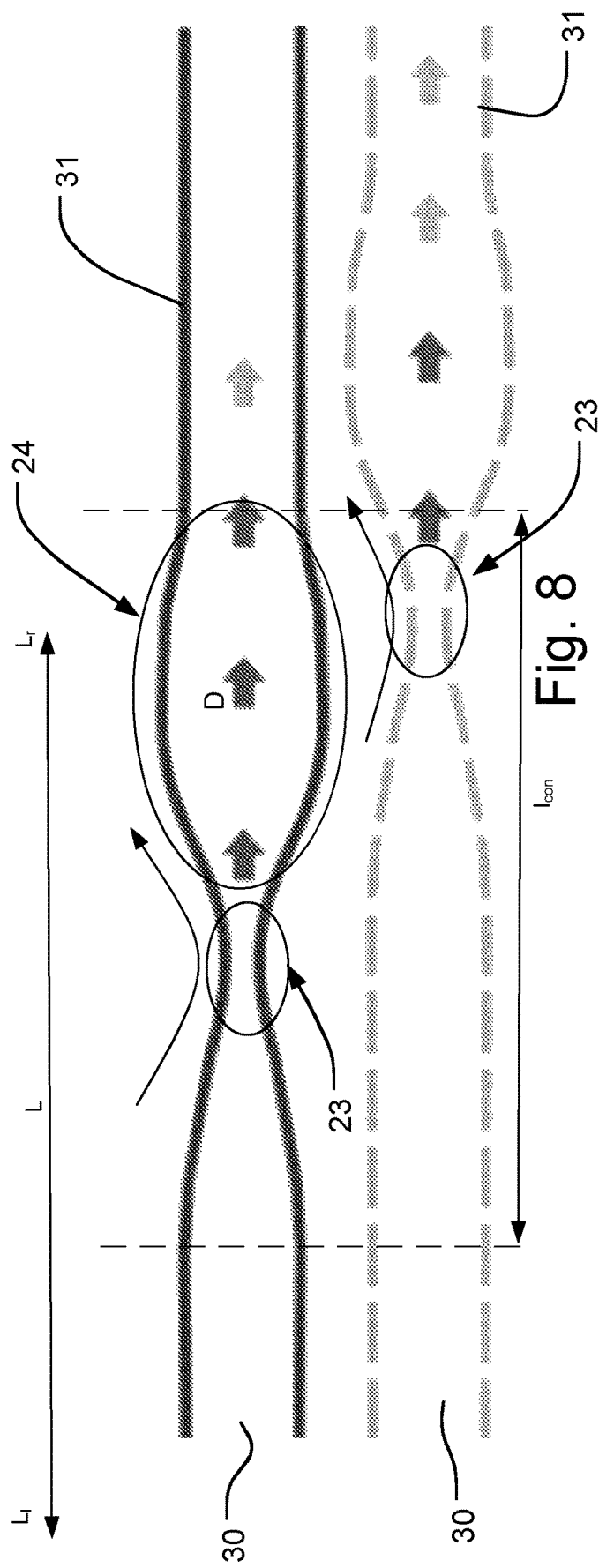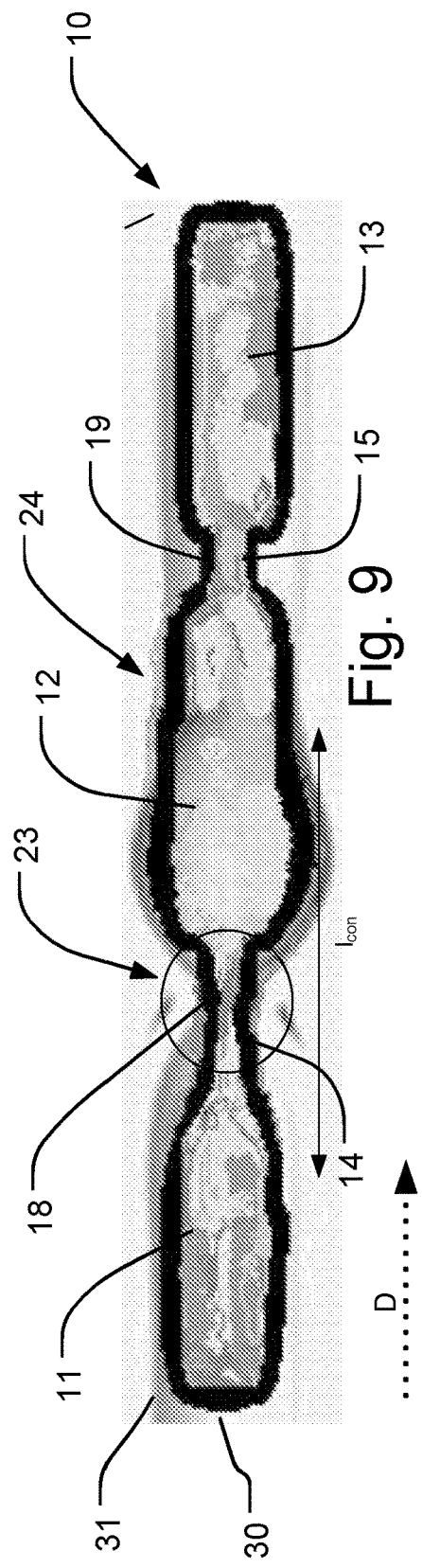
Fig. 8
Fig. 9

OCCLUSION DEVICE FOR REVERSIBLE OCCLUSION OF A BIOLOGICAL TUBE

CROSS-REFERENCE TO RELATED APPLICATIONS

The present application is a 371 national phase filing of International Application No. PCT/DK2016/050129, entitled "OCCLUSION DEVICE FOR REVERSIBLE OCCLUSION OF A BIOLOGICAL TUBE", filed 12 May 2016, which claims priority to European Patent Application No. 15167312.6, entitled "OCCLUSION DEVICE FOR REVERSIBLE OCCLUSION OF A BIOLOGICAL TUBE", filed 12 May 2015.

BACKGROUND

The present disclosure relates to an occlusion device for blocking a biological tube, the biological tube being prone to a peristaltic wave having a wave length, where the occlusion device is divided into at least two sections, and each section is connected by at least one narrowing to at least one other section. The occlusion device should be understood to be used in occlusion of the biological tube, especially the device is intended to be used in contraception of an animal species, such as in a human or animal body.

More specifically the disclosure relates to contraception of female and/or male gendered species, which is often achieved by methods of surgery, intervening with the biological tube, which are responsible for transportation of fertility fluids, such as the transportation of spermatozoes or oocytes in for example the human reproductive system. In humans the biological tube, which contributes to the transportation of for example spermatozoes or oocytes is the vas deferens in males, and fallopian tube in females. Further to surgery methods, contraception methods today also include the intake of hormones, or the insertion of a device occluding, such as blocking at least a part of the biological tube.

The most normal method of contraception for especially the male gender is sterilisation, which is achieved by means of surgery. Contraception of the female gender includes both methods of surgery and hormones. For both genders several different methods of surgery introducing a blocking element in the biological tube for contraception exist, which prevents effectively the risk of getting unintended pregnant. However, most known contraception methods and devices used, often intervenes with the biological tube in such a destructive manner, epically due to incisions in the tissue of the biological tube, that the possibility of having the occlusion device removed and the tissue re-established without damaging the natural behaviour of the tissue in the biological tube is a problem. The result often being that the normal behaviour of the tissue of the biological tube is destroyed to such a degree that the reproductive system of especially the male gender is impaired.

With regards to fertility limitation or sterilization a total blocking of the biological tube is important since a single fertility cell, such as spermatozoes leaving the biological tube of for example the male reproductive system may lead to pregnancy during intercourse. Most often the preventive methods, as previously described is non-reversible or reversible with the risk of damaging the biological tube due to the surgery.

The preferred method of sterilisation of especially men is to perform a vasectomy. This is a surgical method, where the vas deferens of the male reproductive system is cut and tied off thereby preventing spermatozoes from entering into the seminal vesicles, from where they would normally be ejaculated during intercourse. A vasectomy may be reversed, however this procedure requires surgery which is often problematic and expensive. That is the biological tube should in the case of the human male be understood as being the vas deferens of the male reproductive system. However, within the meaning of this disclosure, a biological tube shall refer to any tube, duct, passage or any other structure, not specifically mentioned, which carries gas, fluids or solids in a biological system such as in humans and animals. The understanding of a biological tube should thus not be limited to the vas deferens of the male gender, but also constitutes for example the biological tubes of the female reproductive system and other biological tubes within a species which have the properties to perform peristaltic wave motions for transportation of objects, fluids or other kinds of structures.

The length between the last position before a contraction in which a biological tube has a diameter corresponding to its diameter in a relaxed or resting condition and the first position after an expansion in which the bio-logical tube resumes the diameter corresponding to its diameter in a relaxed or resting condition, when seen in a direction opposite to the movement of a peristaltic wave, can be measured and is in this disclosure denoted as the wavelength of a peristaltic wave.

One reason as to why a surgery method, such as a vasectomy is the preferred method of male sterilization is explained in the following. Similar to other biological tubes, the vas deferens uses so called peristaltic motions for the transportation of spermatozoes out of the vas deferens. The peristaltic motion is in principle characterized as a wave movement arising in the bio-logical tube due to the smooth muscle tissue creating contractions of the bio-logical tube. By the peristaltic wave movement provided by smooth muscle tissue of the vas deferens, spermatozoes is transported out of the vas deferens into the seminal vesicles from where they are ejaculated. The forces of transportation created by the peristaltic wave contractions of the biological tube, creates some requirements to the method of blocking or the blocking element inserted into the vas deferens for preventing the spermatozoes from being transported out of the vas deferens. A simple insertion of a blocking device might lead to the device being pushed out of the vas deferens along with spermatozoes as a result of the forces of the peristaltic wave contraction pushing the blocking element out of the vas deferens, if not tightly fixed at the place of insertion. Therefore the most preferred method is to perform a vasectomy, by which the tissue layers, including the smooth muscle tissue of the vas deferens is cut and tied, so that the transportation of the spermatozoes out of the vas deferens is prevented.

This method however, results in a problematic re-establishment of the male reproductive system after a vasectomy has been performed, since several tissue layers of the vas deferens has to be restored and reconnected. Especially the reconnection of the cut muscle tissue is of great importance for restoration of the ability of the biological tissue to produce a peristaltic wave causing the transportation of spermatozoes. If the tissue of the vas deferens is not sufficiently restored, the male remains sterile despite the effort of restoring the normal function of the vas deferens. Currently is has been found that more than 30% of all restored vasectomies is unsuccessful, resulting in the male staying sterile despite the effort of restoration.

Methods, which more successfully provides for a reversible blocking of the vas deferens, have therefore been introduced throughout the years, such as the insertion of an occluding element. By using an occluding element instead of for example performing a surgery method, the blocking of the biological tube is more easily reversed. This is due to the fact that only a minor surgery intervention of the tissue of the biological tube, for insertion of the occluding element, is necessary.

One such blocking device is described in U.S. Pat. No. 3,648,683, which describes a device for blocking a biological tube, in this case the vas deferens. The device comprises a series of sections of blocking members of different sizes, which are joined together by linking means. The different sizes of the blocking members, provides for a device, fitting different sized diameters of the biological tube. The device is intended to be inserted in its full length with all the blocking members intact into the vas deferens, so that the proper size is selected as being the one that fits most snugly in the lumen of the vas deferens. The blocking member(s) that remain(s) after finding the one(s) that fills the vas deferens completely are broken off at the linking member, and the blocking members inserted in the vas deferens are tied to the vas deferens by means of for example surgery. For insertion of the blocking members an incision is made in the tissue of the vas deferens.

Further to the drawbacks already previously described in relation to the prior art occlusion devices, even if being described as being reversible, does require surgery intervention of the tissue of the biological tube, which provides the risk of destroying the physiological behaviour of the biological tube, such as the peristaltic motions of the vas deferens, limiting the chances of successfully reversing the contraception.

SUMMARY

It is therefore an object of the present disclosure invention to provide an occlusion device which overcomes the previously described drawbacks of known reversible occlusion devices for a biological tube.

This is achieved by providing an occlusion device for blocking a biological tube, said biological tube being prone to a peristaltic wave having a wave length, where said occlusion device comprises at least two sections, each section having a length, lsec, where each section is connected by at least one narrowing having a length, lnar, to at least one other section, where a diameter, dnar, of said narrowing is smaller than the diameter, dsec, of at least one of said two sections wherein that said occlusion device comprises an elastic material, and that each section is configured to deform in accordance with a force applied by said peristaltic wave, and that the length of at least one of said at least two sections corresponds substantially to the wave length of said peristaltic wave in said biological tube, so as to absorb said peristaltic wave.

With this construction of the occlusion device, the occlusion device in itself when inserted into a biological tube, such as the vas deferens, is able to withstand the contraction forces applied during a peristaltic wave contraction of the biological tube.

In the scope of this disclosure invention the diameter, dnar, of said narrowing is defined as the smallest diameter of said narrowing. Likewise the diameter, dsec, of said section is defined as the maximum diameter of said section.

Depending on the shape of the occlusion device a section may be defined as a continuous part of the occlusion device having the same maximum diameter across the length of said section, and thus the narrowing may be defined as beginning when the size of the diameter begins to decrease and the end of the narrowing being when the diameter has reached the maximum diameter, thus a new section begins.

In the scope of this disclosure invention the wording "absorb" in relation to a peristaltic wave or other movement is intended to mean that the device is able to withstand the movement and/or passing of the peristaltic wave whilst remaining substantially in the same position in the biological tube.

The occlusion device may be divided into at least two sections, where each section is connected by at least one narrowing to at least one other section, and where a diameter, dnar, of said narrowing is smaller than the diameter, dsec, of at least one of the two sections, and said two sections is substantially of the same length, lsec, wherein the occlusion device is of an elastic material, and that each section is configured to deform in accordance with a force applied by the peristaltic wave, and that the length of each of the at least two sections corresponds substantially to the wave length of the peristaltic wave in the biological tube, so as to absorb the peristaltic wave. With this construction of the occlusion device, the occlusion device in itself when inserted into a biological tube, such as the vas deferens, is able to withstand the contraction forces applied during a peristaltic wave contraction of the biological tube. The design with at least two sections made of an elastic material together with the narrowings, has the effect of keeping the occlusion device in place during the propagation of the peristaltic wave along the biological tube. That is, as the peristaltic wave moves along the biological tube, one section at a time is influenced by the contraction, while the remaining sections withstands the forces, and thus keeps the device in its original position of insertion within the tube. Within the meaning of withstand, it should be understood that the sections and the narrowings is constructed from a material and designed with dimensions, which makes the occlusion device able to let the peristaltic wave pass one section at a time, while distributing the forces applied from the peristaltic wave contraction along the length of the occlusion device. Thus as it will appear in the following, the occlusion device is able to deform in the sense of adapt in shape in order to withstand the forces arising from the peristaltic contractions within the biological tube. The properties of the device will become apparent throughout the description and is described in more detail in the detailed part of the description.

For the device to properly absorb the peristaltic wave so as to be kept in place, the sections of the occlusion device is in a development of the occlusion device, constructed so that the length of each of the at least two sections is substantially the length of a peristaltic wave arising in the biological tube, preferably the vas deferens during transportation of spermatozoes through the vas deferens.

In general a peristaltic motion is characterized by a wave of distention causing the tissue to relax followed by a wave of contraction creating a force, which pushes a structure, object and/or fluid along the biological tube. The length of the peristaltic wave should thus be understood as the length between two local contractions of the smooth muscles tissue forcing the structure within the biological tube to move. Thus the occlusion device is designed such that a length of a section substantially matches the length between two local contractions.

Furthermore, the at least two sections is made from an elastic material, and configured so that each section, independently from the other sections, is able to expand and deform under influence from the applied biological pressure and/or contraction along the length of said occlusion device, such as the peristaltic wave of the vas deferens.

That is the two sections and said narrowing are configured so that at least one section expands under influence from said applied biological pressure and/or contraction of said biological tube, so that said occlusion device substantially stays in a place of insertion within the biological tube. That is the section which is not directly under influence from the propagation of the peristaltic wave, together with the narrowing takes up the forces applied to the section under influence. That is the sections, not under influence experiences a slight expansion pushing the walls of the occlusion device into the membrane wall of the inner lumen of the biological tube, so as to tighten the fit to the lumen.

With regards to the dimensions of the occlusion device, it is of importance that the device is constructed so as to fit into the biological tube and to match the type of movement in said tube, since the movement may vary with each biological tube and with time. Thus, in an example embodiment, where the device is to be used in for example the vas deferens of the male reproductive system, the device is designed such that the ratio between the diameter of at least one of the two sections and the narrowing dsec/dnar is approximately 1 to 4, preferably approximately 1 to 3 and more preferred approximately 2. However other ratios between the narrowings and the sections may be more preferred depending on the biological tube.

The largest diameter of the occlusion device preferably corresponds substantially to the inner diameter of the vas deferens, which however, may vary from male to male, why the two sections comprises an outer diameter being substantially the size of the inner diameter of said biological tube, preferably said outer diameter of said two sections is in the range of approximately 0.1-0.65 mm in diameter, and wherein said narrowings have a substantially smaller diameter than that of said two sections, preferably the diameter of said narrowings is in the range of 0.05-0.30 mm in diameter.

The at least two sections is of substantially same length. Preferably each of said at least two sections is in the range of approximately 1.5-3.5 min in length. Said narrowing preferably is in the range of 0.3-0.9 mm in length.

In a similar manner, the length of each of the sections of the device should preferably correspond to the length of the peristaltic wave as previously described. The length of each of said at least two sections is substantially the wavelength of a peristaltic wave arising in the biological tube, preferably in the vas deferens, during transportation of spermatozoes through the vas deferens. Furthermore, the length of said at least one narrowing may likewise be substantially the wavelength of a peristaltic wave arising in the biological tube, preferably in the vas deferens, during transportation of spermatozoes through the vas deferens.

The length of each section may vary depending on the size of the biological tube to which it is inserted into, such as the vas deference, and should therefore not be limited to the dimension given herewith.

However, in an example embodiment the length, lnar of said narrowing is smaller than the length, lsec, of said sections, such that a ratio between the length of at least one of the two sections and said narrowing is approximately lsec/lnar≥3. Preferably the at least two sections is of substantially the same length, and each of said at least two sections is in the range of approximately 0.9-3.5 mm in length, and said narrowing preferably being in the range of 0.3-1.2 mm in length. Any combination of the lengths and diameter given in the previously described examples of the dimensions of the occlusion device should be understood as to be able to be combined by a skilled person such that the most proper designed occlusion device for a specific purpose, whether inserted into the vas deferens, or other biological tubes could be achieved.

As previously described, the occlusion device is intended for insertion into a biological tube, preferably reversibly inserted such that it may be removed without substantially damaging the biological tissue of the biological tube. Thus in a preferred embodiment the occlusion device is releasable from said biological tube, so that it is configured to be removed after use without substantially damaging the biological tube. Within the meaning of the wording releasable, it should be understood that the occlusion device is configured to be loosened or simply pulled out of the biological tube to which it is inserted, without substantially damaging the tissue of the tube.

As will become apparent throughout the description, the material chosen for the occlusion device may thus comprise material properties making the device releasable. However, the material chosen should be such that the device may still withstand the forces applied to the occlusion device under influence from a peristaltic wave motion.

The outside of the occlusion device being in contact with the biological tube when the device is inserted may in itself be biocompatible or be coated with a biocompatible material.

Furthermore in one development of the device the at least two sections and the narrowing each comprises a hollow interior, which are interconnected so as to allow for passage of a material constrained within the total length of said occlusion device. The occlusion device may in this way be filled with a biocompatible material before or after insertion into the biological tube as will be apparent in the following.

In another development the occlusion device comprises at least one hollow interior arranged in at least one of said sections and/or said narrowings.

In another example embodiment the occlusion device comprises at least two hollow interiors arranged in at least one of said sections and/or said narrowings, where said at least two interiors are separate interiors not being in open connection with each other.

Preferably the occlusion device is substantially tubular in shape, however other shapes such as triangular, rectangular or similar shapes are also possible. In any case, the occlusion device may be hollow or could be filled with a biocompatible material.

For providing an easy insertion of the occlusion device into the biological tube, the occlusion device is configured to be in a first state having a first volume, and a second state, wherein said occlusion device is expanded to obtain a second larger volume, preferably said expansion is configured to propagate said occlusion device radially. By a radially propagating expansion of the device, the device is equally expanded over its entire length, within the range of expansion of the material. That is the sections of the occlusion device comprise a larger diameter than that of the narrowings. With this construction of the device, it may easily be introduced into any sized biological tube. For the following tight fit inside the biological tube, the occlusion device may also be configured to be inflatable, so that it after insertion is inflated to fit the exact inner diameter of the biological tube. In this way one occlusion device may fit different sized biological tubes, such as different sizes of the vas deferens. However, the device could also be inflated to obtain the second volume prior to insertion.

In any case, whether being inflated prior to insertion or after, the occlusion device is filled with a fluid, gas or a resilient material, such as for example air or silicone. In general the device may be filled with any biocompatible material suitable for insertion into a body part or structure.

In order to enhance the properties, which the occlusion device possess for staying in place within the biological tube, the occlusion device may in one example embodiment be provided with a friction enhancing surface, preferably provided as a roughened, barbed, flanged, threaded and/or ribbed surface or the like, which when inserted into the biological tube is in contact with an inner wall of the biological tube. In this way an increased friction between the occlusion device and the inner wall of the biological tube is obtained, which enhances the ability of the occlusion device to withstand the forces created by the peristaltic wave without damaging the biological tube.

In a further example embodiment of the occlusion device, the surface is treated with a material being inert to the surface of the inner wall of the biological tube, preferably configured to stick, glue or adhere. That is the occlusion device may be treated with a biocompatible material or a combination of biocompatible materials, which for example provides for a mesh into which the tissue of the biological tube could grow. The in-growth should however, preferably be provided in such a manner that the device is easily loosened from the biological tissue for removing of the device, when no longer needed. The in-growth could for example react to a fluid introduced into the biological tube upon removal, whereby the in-growth dissolves, and the device is loosened from the tissue, thereby preventing damage to the tissue upon removal of the device.

The biocompatible material may be selected from the group comprising; polymers such as silicones, rubber, poly (ethylene), poly (vinyl chloride), polyurethanes, polylactides and/or natural polymers such as collagen, gelatin, elastin, silk, polysaccharide.

The biocompatible material may also have a foam shape or like shape with pores and/or cavities wherein the tissue can grow and attach itself.

Furthermore, the surface of the occlusion device is in one example embodiment treated with an antimicrobial agent, so as to provide for protection against infections in the tissue caused by the insertion of the device.

In a further example embodiment of the occlusion device, the device comprises a removal element, said removal element comprising a magnetic material. The removal element may be an elongated element and is preferably arranged in and/or on one of the outermost sections.

The occlusion device may further comprise other materials so that the occlusion device can be readily visible using imaging techniques such as e.g. ultrasound or x-rays.

As described previously, the occlusion device may be used as a blocking means in any biological tube being prone to a peristaltic wave, preferably the device should be used in male contraception, preferably for insertion into the vas deferens or for use in female contraception, preferably insertion into the fallopian tube.

BRIEF DESCRIPTION OF THE DRAWINGS

Examples of the principles of this disclosure will be described in further details with reference to the accompanying drawings.

FIG. 8 illustrates the physiological characteristics of a peristaltic wave of contraction in a biological tube.

FIG. 9 illustrates an occlusion device according to the disclosure, inserted into a biological tube being influenced by a peristaltic wave of contraction.

DETAILED DESCRIPTION

The device according to the present disclosure is in the following explained with regards to the male reproductive system. As already indicated, the device should however not be limited thereto, since it could also be used in for example the female reproductive system and/or the male reproductive system of other species than the human kind, as well as in any other biological tube being prone to especially a peristaltic wave motion.

The device is further in the following described as having three sections, but it is understood that this would also be feasible with at least two sections and is only explained as an example.

Figure 1:
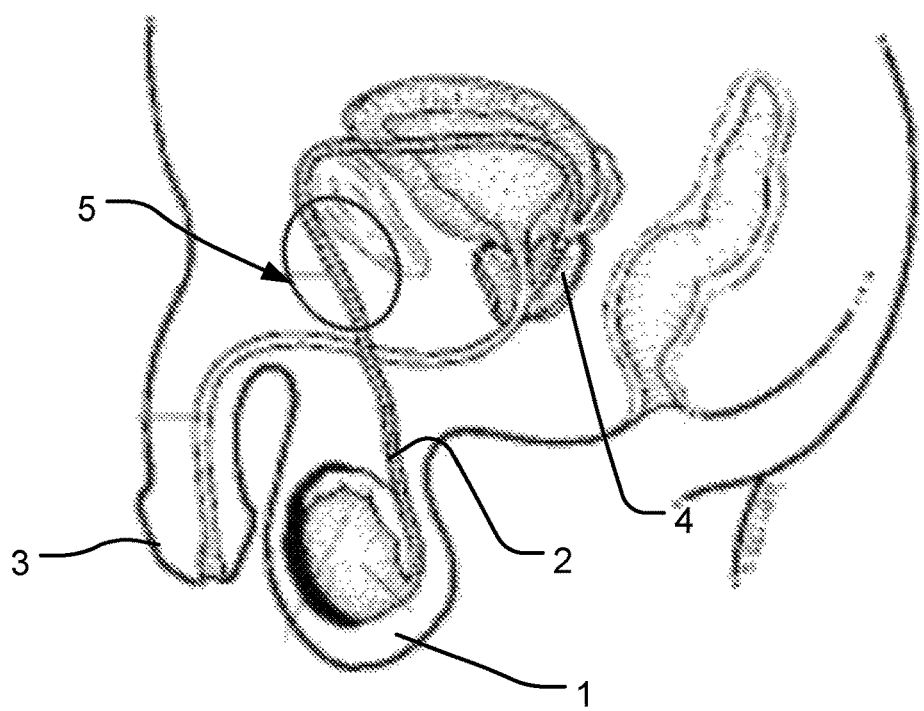
FIG. 1 illustrates a sagittal plane of the male reproductive system, wherein an area of the vas deferens is encircled to illustrate the approximate place of insertion of an occlusion device according to the disclosure.
Figure 2:
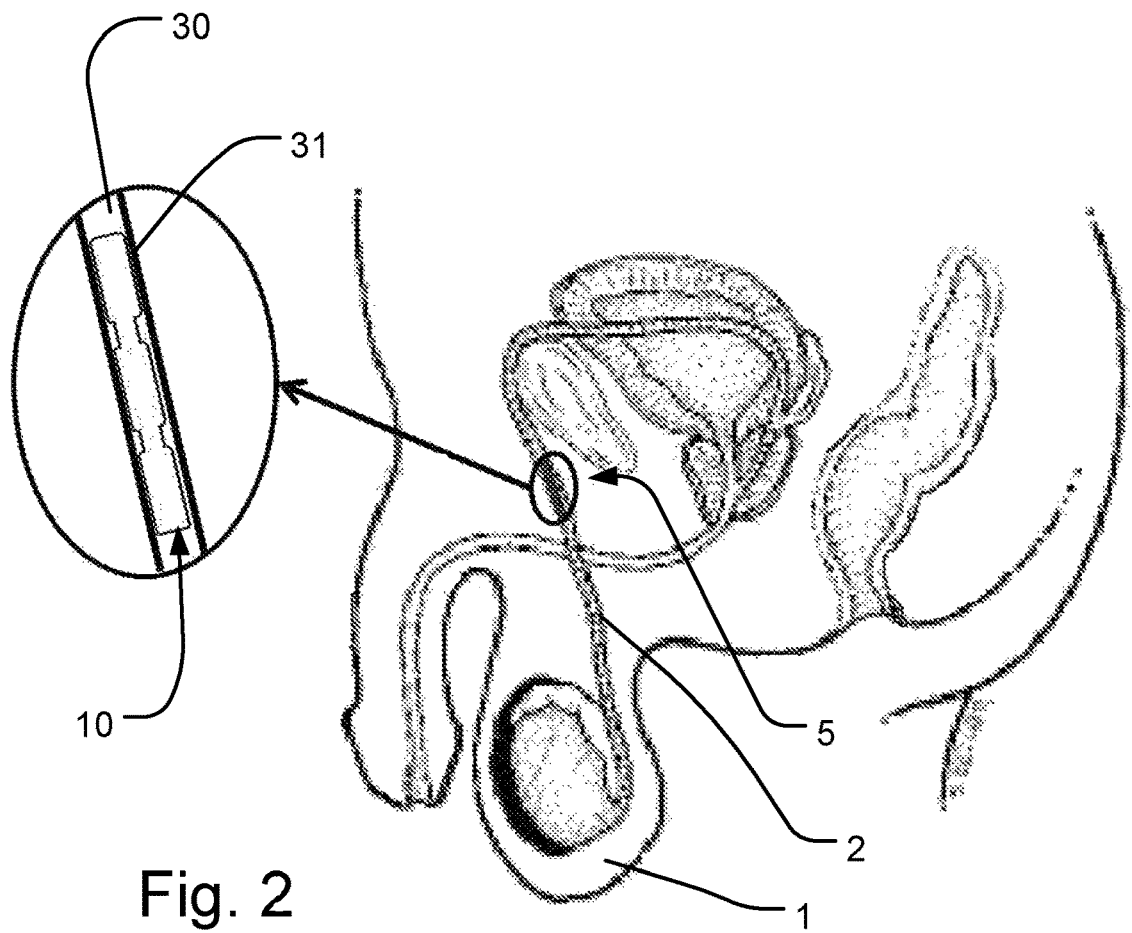
FIG. 2 illustrates the occlusion device according to the disclosure inserted into the area encircled in the sagittal plane of the male reproductive system in FIG. 1.

Referring initially to FIGS. 1 and 2 the human male reproductive system with regards to the mechanisms relevant for the present disclosure will be explained. As illustrated in the figures the male reproductive system of humans comprises among other structures the testis 1, where the spermatozoes are developed, the ductus deferens 2, also called the vas deferens, through which spermatozoes are transported into the ejaculatory duct 4, from where they are ejected through ducts in the penis 3. The transportation of spermatozoes through the vas deferens 2 is achieved due to the tissue properties of the vas deferens. The smooth muscle tissue of the vas deferens creates peristaltic contractions which in peristaltic wave motions transports the spermatozoes towards the ejaculatory duct 4.

In general, as illustrated in FIG. 8, the shown segment of the biological tube defines a longitudinal axis L along which it extends. The fully drawn and dashed drawn biological tubes represent two stages of the same biological tube, shown side by side for illustrative purposes.

The peristaltic wave includes a first wave of relaxation, marked in area 24, which travels along the biological tube in the direction going from Ll to Lr on the longitudinal axis allowing the tissue membrane 31 surrounding the lumen 30 of the biological tube to relax so as to be able to distend. Following this wave of distension, a second wave of contraction, illustrated by the encircled area 23 in FIG. 8, transports the objects, such as fluids in the biological tube, for example the spermatozoes, along the biological tube. As illustrated in FIG. 8, the peristaltic wave provides for local contractions 23 of the smooth muscle tissue. The distance, lcon, should be regarded as the length of the peristaltic wave measured parallel to the longitudinal axis L. That is the local peristaltic contractions propagate along the entire biological tube, whereby the fluids thereof are transported in the biological tube. The properties of the tissue membrane 31 in the vas deferens 2 of the male reproductive system allows for this peristaltic wave contraction in order to transport spermatozoes from the testis 1 through the vas deferens 2 towards the ejaculatory duct 4.

In contraception, especially the sterilization of men, the vas deferens 2 is as described in the introductory part often cut and tied off or blocked by the insertion of a device, which are tied by surgery to the tissue of the vas deferens to be kept in the position originally inserted. Most often such intervention in the biological tube of the vas deferens in done in the area 5 encircled in FIGS. 1 and 2.

With respect to the above described function of the vas deferens, the occlusion device of the present disclosure and its functionality will be described in more detail with reference to the accompanying figures.

Initially the construction of the occlusion device 10, illustrated in FIGS. 3 and 4, will be explained in detail. As is seen from the figures, the occlusion device 10 is divided into at least three sections 11, 12, 13, where each section is connected by at least one narrowing 14, 15 to at least one other section. That is a first section 11 is connected to a second section 12 by a first narrowing 14 and the second section 12 is further connected to a third section 13 by a second narrowing 15. The device is closed off in both ends 16, 17 so as to define a total length of the device ltot.

Figure 3:
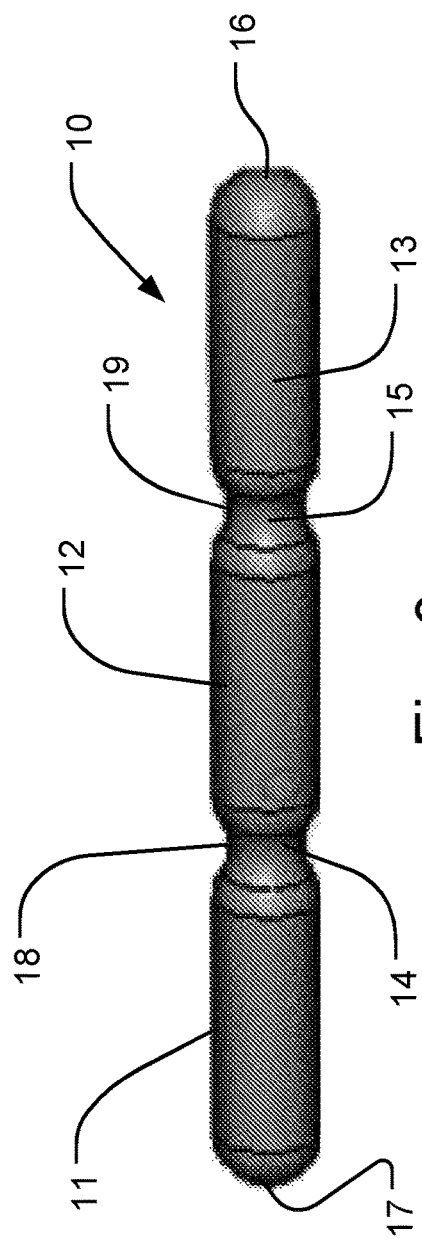
FIGS. 3 and 4 shows an example of the occlusion device according to the disclosure.

Especially illustrated in FIG. 3, the diameter, dnar, of a narrowing 14, 15 is in one example smaller than the diameter, dsec, of at least one of the three sections 11, 12, 13. Furthermore, the three sections 11, 12, 13 is substantially of the same length, lsec, and the narrowing is of a length, lnar, which in the example shown is substantially smaller than the length of at least one of the three sections 11, 12, 13. However, the narrowings and the sections could also be provided in the same length. The disclosure should therefore not be limited to an occlusion device with the specific length dimensions just described in this specific example.

The occlusion device is furthermore of an elastic material, and each section 11, 12, 13 is configured to deform in accordance with a force applied by the peristaltic wave. In order to optionally absorb the peristaltic wave contraction, the length of each of the at least three sections 11, 12, 13 corresponds substantially to the wave length, lcon, of the peristaltic wave in the biological tube of the vas deferens, as illustrated in FIG. 9. With this construction of the sections 11, 12, 13 of the device, one section at a time will mainly be influenced by the peristaltic wave at a certain time, while the remaining two sections are slightly expanded, having the effect of holding the device in place. In this way the forces applied to the occlusion device from the peristaltic wave is therefore not enough to push the device out of place and the device therefore remains in its originally placed position in the vas deferens during the passing of the peristaltic contractions of the vas deferens.

Figure 5:
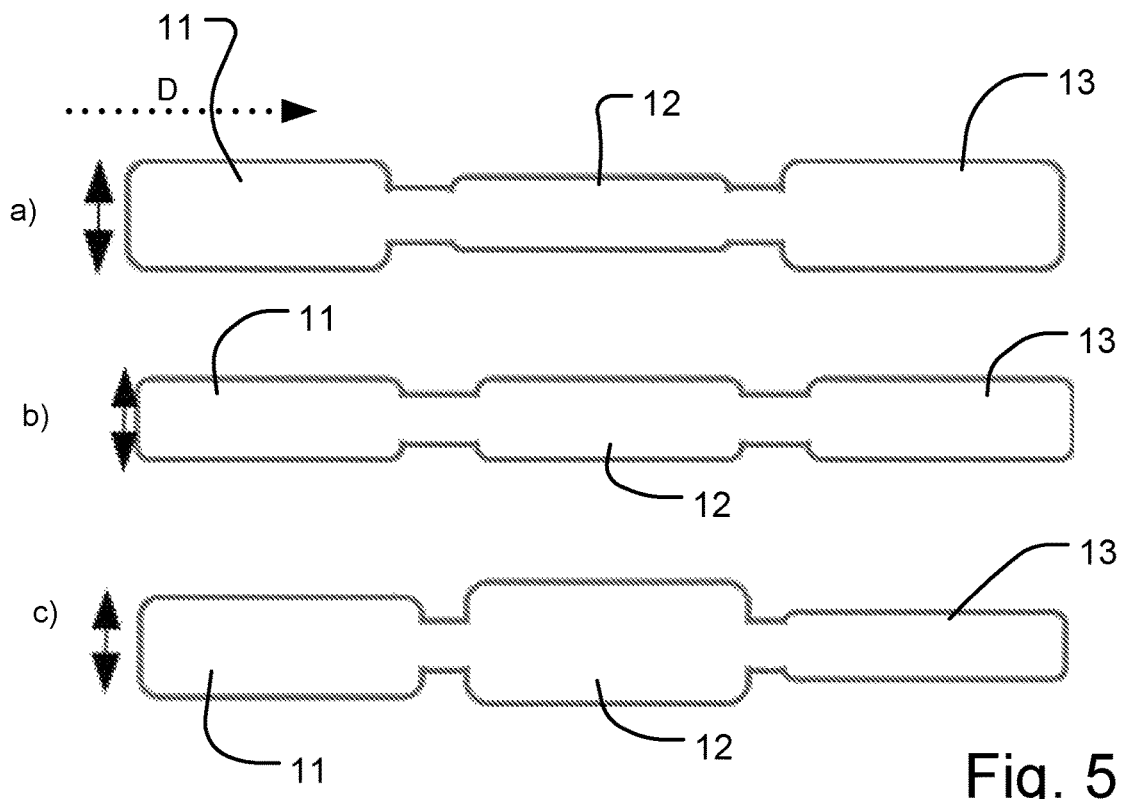
FIGS. 5a through 5c illustrates the elastic properties of the occlusion device, according to an example of the disclosure.

The device is thus designed with each of the three sections 11, 12, 13 of the occlusion device being made from an elastic material, and configured so that each section, more or less independently from the other sections, is able to expand and deform under influence from said applied biological pressure and/or contraction along the length of the occlusion device, such as the peristaltic wave of the vas deferens, as illustrated schematically in FIG. 5. In FIG. 5 the elasticity of the occlusion device is illustrated. A substantially relaxed state of the occlusion device, i.e. a state where the occlusion device is not influenced by a peristaltic wave contraction, is illustrated in FIG. 5b, where the three sections are of substantially the same size.

During propagation of a peristaltic wave for example in the direction of arrow D, as illustrated in FIGS. 5a and 5c it is seen how the sections are able to deform and thus vary in diameter due to the forces applied from the propagation of the peristaltic wave. It is seen in the Figures how the sections may expand due to the elastic material from which the occlusion device is made. A slight expansion of the occlusion device during the peristaltic wave propagation only enhances the effect of keeping the occlusion device in place within the vas deferens, since the expanded walls of the occlusion device of FIGS. 5a and 5c creates a force against the inner membrane wall of the vas deferens. In general the occlusion device preferably returns to its original dimensions of FIG. 5b after the passing of a peristaltic wave. The elasticity of the device furthermore makes the occlusion device more fitting within the vas deferens or any other biological tube, since it by its elastic properties is able to adapt to the lumen into which it is inserted.

Furthermore, the three sections 11, 12, 13 and the narrowings 14, 15 are configured so that at least two section are able to slightly expand under influence from the applied biological pressure and/or contraction of said biological tube, so that the occlusion device substantially stays in a place of insertion within said biological tube. The narrowings however together with the sections, could provide for a flow of fluid or similar material within the hollow interior of the device, enhancing the effect of absorbance, since the fluid in this way is distributed within the occlusion device, as is also schematically illustrated in FIG. 5.

The behaviour of the occlusion device in the biological tube, in this case the vas deferens, is in more detail, with reference to the general principle of a peristaltic wave contraction of FIG. 8, illustrated in FIG. 9. In FIG. 9, the occlusion device is shown inserted into the lumen 30 of a biological tube, being under influence of a peristaltic wave propagating in the direction of arrow D. As is illustrated in the figure, the middle section 12 of the occlusion device 10 reacts to a relaxation of the membrane 31 of the biological tube, thus reacting to the wave of distension of the peristaltic wave. The following wave of contraction especially influences the narrowing 14 of the occlusion device 10, which reacts to the local contraction of the peristaltic wave 23. In this way the narrowing 14 and section 12 together absorbs the peristaltic wave while distributing the forces of the contractions along the occlusion device so that the sections 11, 13 are slightly expanded during the propagating of the peristaltic wave, keeping the device in place. The following further contraction, not illustrated, in a similar manner influences section 13 and narrowing 15, while section 11 and 12 remains substantially uninfluenced by the contraction so as to keep the occlusion device in place within the biological tube.

In more detail the occlusion device is thus designed such that the length of each of said at least three sections is substantially the length of a peristaltic wave arising especially in the biological tube of the vas deferens during transportation of spermatozoes through the vas deferens. This special design makes the device capable of withstanding not only the forces from the peristaltic wave but also the pressure of the transportation of spermatozoes out of the vas deferens.

The occlusion device is furthermore designed with dimensions which fit into the lumen of the vas deferens. The lumen of the vas deferens is on average approximately 0.3 mm in diameter but may vary from male to male, why the occlusion device, to fit tightly into the lumen in order to block the transportation of spermatozoes, is designed with a small oversized dimension within a range from a smallest to a largest outer diameter. That is the outer diameter of the three sections 11, 12, 13 is substantially the size of the inner diameter of the biological tube, i.e. the lumen of the vas deferens. Preferably the outer diameter of the three sections is in the range of approximately 0.1-0.65 min in diameter.

When the occlusion device is designed for insertion into the vas deferens, the outer diameter of the three sections is preferably slightly larger than the inner diameter (i.e. the lumen) of the vas deferens to ensure a tight fit therein.

Accordingly, the narrowings are configured to provide the device with a stretching effect, such that the narrowings 14, 15 elastically lets the peristaltic wave pass onto the next section 11, 12, 13 of the occlusion device. Thus, the narrowings 14, 15 have a substantially smaller diameter than that of the three sections; preferably the diameter of the narrowings is in the range of 0.05-0.3 mm in diameter.

The ratio between the diameter of at least one of the three sections and the narrowing is approximately dsec/dnar≥2, and the ratio between the length of at least one of the three sections and the narrowing is approximately lsec/lnar≥3.

Furthermore as is seen from the figures the at least three sections 11, 12, 13 is of substantially same length, preferably the at least three sections is in the range of approximately 0.9-3.5 mm in length, and the narrowing is of a length substantially smaller than at least one of said three sections, preferably said narrowings is in the range of 0.3-1.2 mm in length. The transition between a section 11, 12, 13 to a narrowing 14, 15 is constructed as a smooth gradual narrowing, which form the transition from the connection of a narrowing to a section 11, 12, 13 which decreases in diameter so as to provide a valley 18, 19. That is the diameter of the narrowings varies along its length to provide for the valley 18, 19 between two sections. With this design of the device, the narrowings being able to pull back on the sections during passing of a peristaltic wave, having the effect that the sections not influenced by the peristaltic wave, is kept in place.

As is illustrated in the figures the occlusion device is substantially tubular in shape, which fits the interior lumen of the vas deferens.

Figure 10:
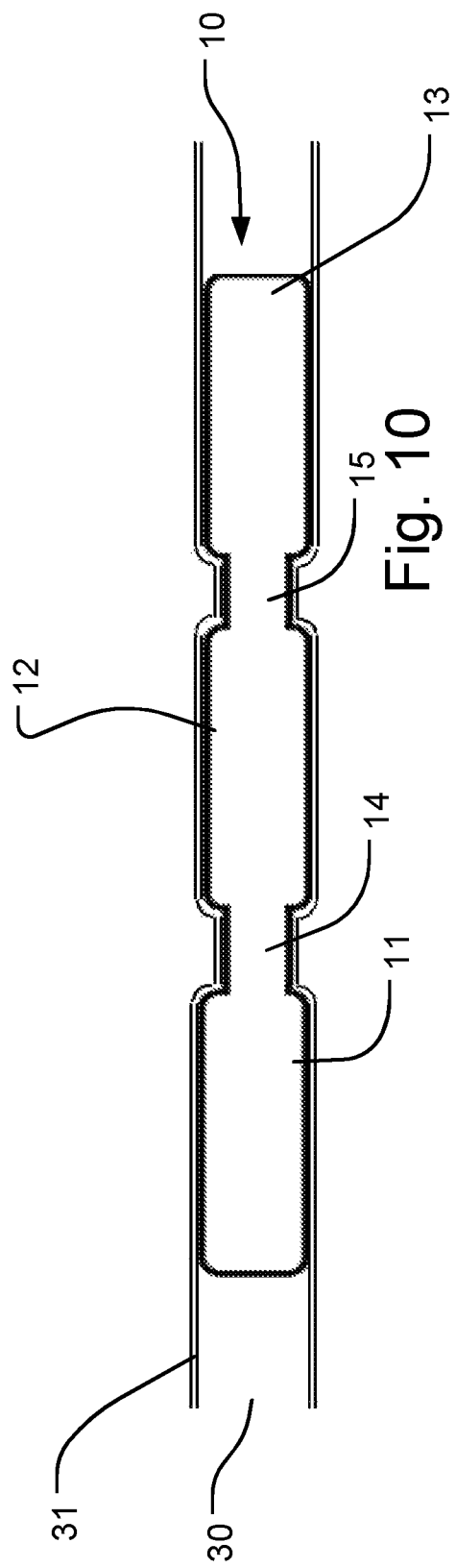
FIG. 10 schematically illustrates an occlusion device according to the disclosure inserted into a biological tube.

In general the occlusion device is designed so that the outer wall of the device fits the membrane 31 of the biological tube, such as the vas deferens. That is, as illustrated especially in FIG. 10, when the device is inserted into the biological tube, membrane 31 of the biological tube adapts to the occlusion device, so as to follow the structures thereof. Thus, the three sections 11, 12, 13 is tightly surrounded by the membrane and the tissue furthermore also adapts so as to tightly surround the narrowings 14, 15 of the occlusion device.

Figure 4:
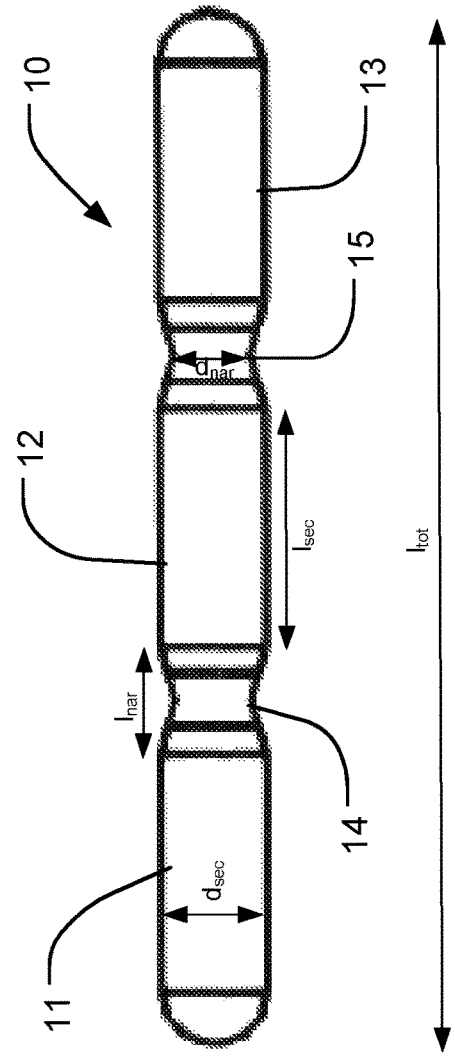
Figure 7A:
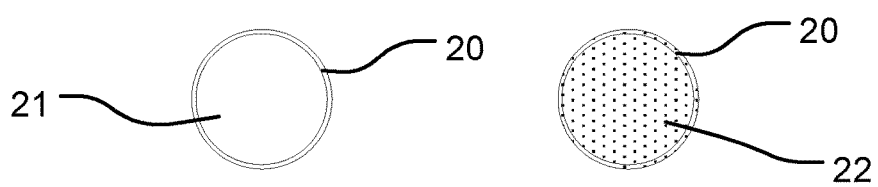
FIGS. 7a to 7b illustrates a cross-section of said occlusion device according to an example of the disclosure.

According to an example of the disclosure, for example the occlusion device of FIGS. 3 and 4, the sections 11, 12, 13 and narrowings 14, 15 of the occlusion device, defines hollow elements of the occlusion device. That is each section 11, 12, 13 and narrowing 14, 15 is provided with a hollow interior 21. The hollow elements are preferably interconnected so as to allow for passage of a material constrained within the total length of said occlusion device. That is, as illustrated in the cross section of FIGS. 7a and 7b, the occlusion device comprises an outer membrane 20 and a hollow interior 21.

In one example the occlusion device according to for example FIGS. 3 and 4, is configured to be in a first state having a first volume, and a second state, wherein the occlusion device is expanded to obtain a second larger volume, preferably the expansion is configured to propagate the occlusion device radially. That is, prior to insertion or after insertion into the vas deferens, the occlusion device may be in a first collapsed state, in which the occlusion device comprises a collapsed hollow interior intended to be expanded to an enlarged second state having the second volume. With an expandable occlusion device, the insertion thereof into the biological tube, of for example the vas deferens is easily obtained. The occlusion device may thus be inserted prior to expansion of the hollow interior, where the resistance against the lumen 30 of the vas deferens is minimized. After insertion the occlusion device is thus expanded so as to tightly fill out the lumen of the vas deferens.

The occlusion device may also be expanded to the second volume before insertion, for example during production and/or prior to packing and delivery thereof. In each case, the expansion of the occlusion device to provide the second volume is obtained by the occlusion device being configured to be inflatable. Other means for reaching the expanded volume is by filling the device with a biocompatible material.

Figure 7B:
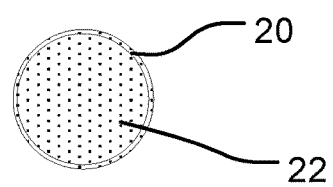

Thus, in one example the hollow interior is filled with a fluid, gas and/or a resilient material 22 as illustrated in FIG. 7b, such as for example air, silicone or similar biocompatible material, before and/or after insertion and/or inflation of said occlusion device. The occlusion device could for example be filled with water or a physiological saline solution (0.9%), which comprises the same osmotic pressure as blood serum. In either case at least one end 16, 17, is in one example provided with a structures providing for the intake of a biocompatible material.

Figure 6:
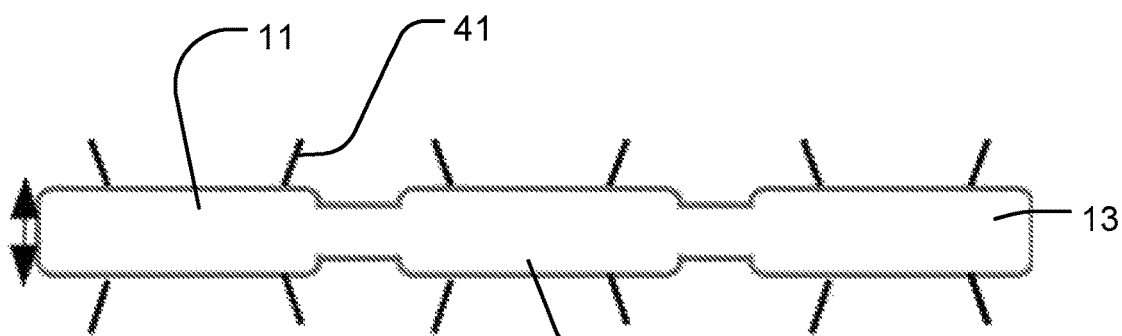
FIG. 6 illustrates the occlusion device according to an example of the disclosure, where the occlusion device is provided with friction enhancing means.

In another example the surface of the occlusion device is provided with a friction-enhancing surface, preferably provided as a roughened, barbed or ribbed surface, being in contact with an inner wall of said biological tube, as is illustrated in FIG. 6, wherein the occlusion device is provided with baffles 41. With a friction enhancing surface of the device, an anchoring effect to the lumen 30 of the vas deferens is achieved, thereby improving the occlusion device ability to stay in place after insertion into the biological tube.

In a further development, the surface of the occlusion device is treated with a material being inert to the surface of the inner wall of the vas deferens, preferably configured to stick, glue or adhere.

Since the device is to be inserted into a biological tube, the occlusion device should be biocompatible since the material chosen for the device should not be rejected, nor attacked by the immune system of the body to which it is inserted. Furthermore, when inserting devices into a body structure, the risk of infections always exist, why the surface of the occlusion device may be treated with an antimicrobial agent, such as silver. In this way the device is resistant towards bacteria, vira and fungi. Additionally the surface of the occlusion device could be produced with a bioabsorbent material, which dissolves over time, by which the tissue of the lumen of the biological tube is allowed to grow into the device.

In one example the occlusion device comprises a removal element, said removal element comprising a magnetic material. The magnetic material may be any material, combination of materials or alloy having magnetic properties. Examples of such are; iron, cobalt, nickel.

In the scope of this disclosure the term magnetic material covers both materials that produce their own persistent magnetic field even in the absence of an applied magnetic field and materials that produce a magnetic field in response to an applied magnetic field.

The removal element may be arranged in just one of the at least two sections. The removal element may also be arranged in a plurality of the sections.

In one example the removal element is in the form of magnetic particles. The magnetic particles may be arranged in the outer membrane of the occlusion device.

In another example the removal element is an elongated element. The removal element may be in the shape of a cylinder and is preferably arranged in one of the sections.

The removal element may be arranged in the hollow interior of a section and/or a narrowing.

The removal element may also extend through the length of the occlusion device in the longitudinal direction.

Figure 11:
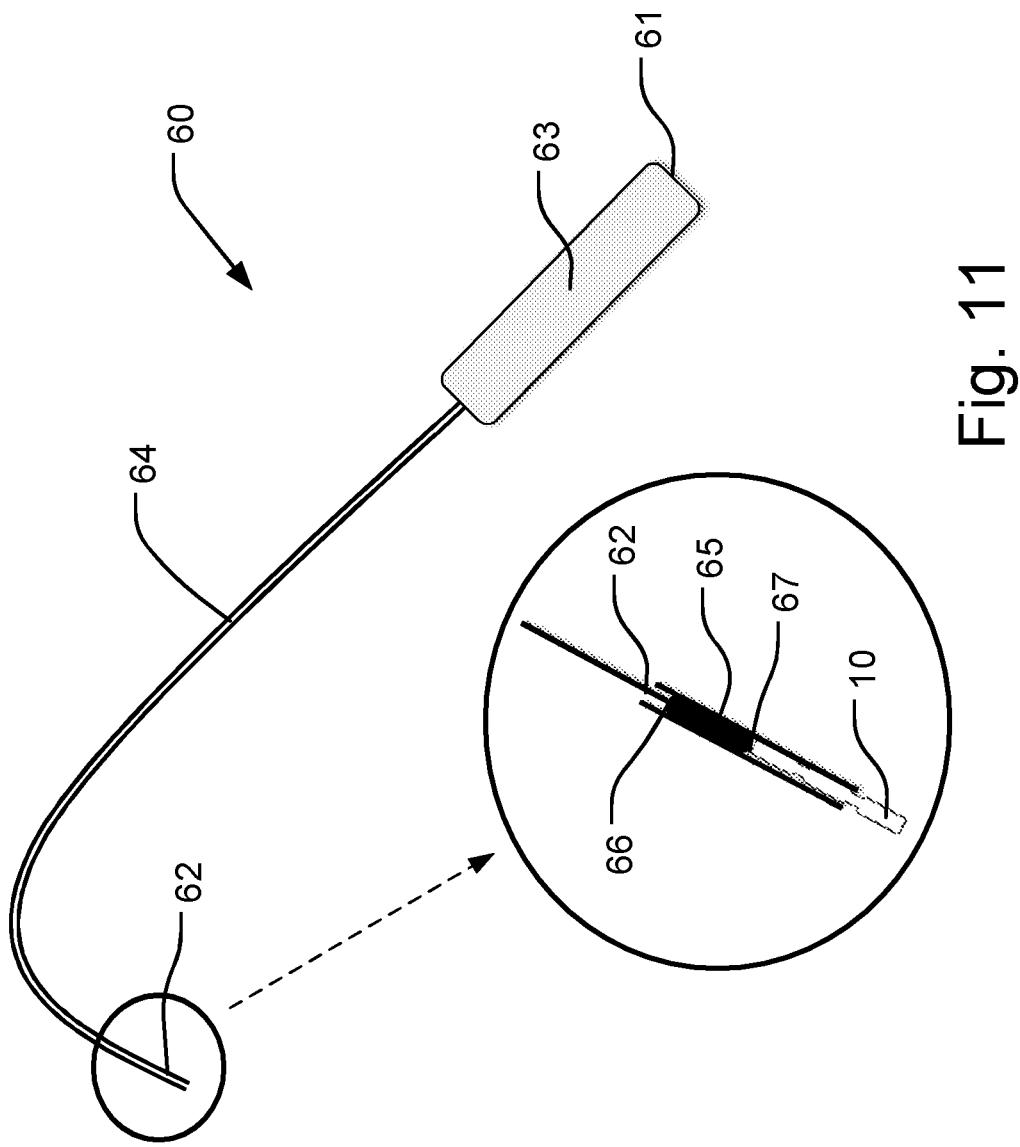
FIG. 11 illustrates a schematic drawing of an insertion device having the occlusion device attached.
Figure 12:
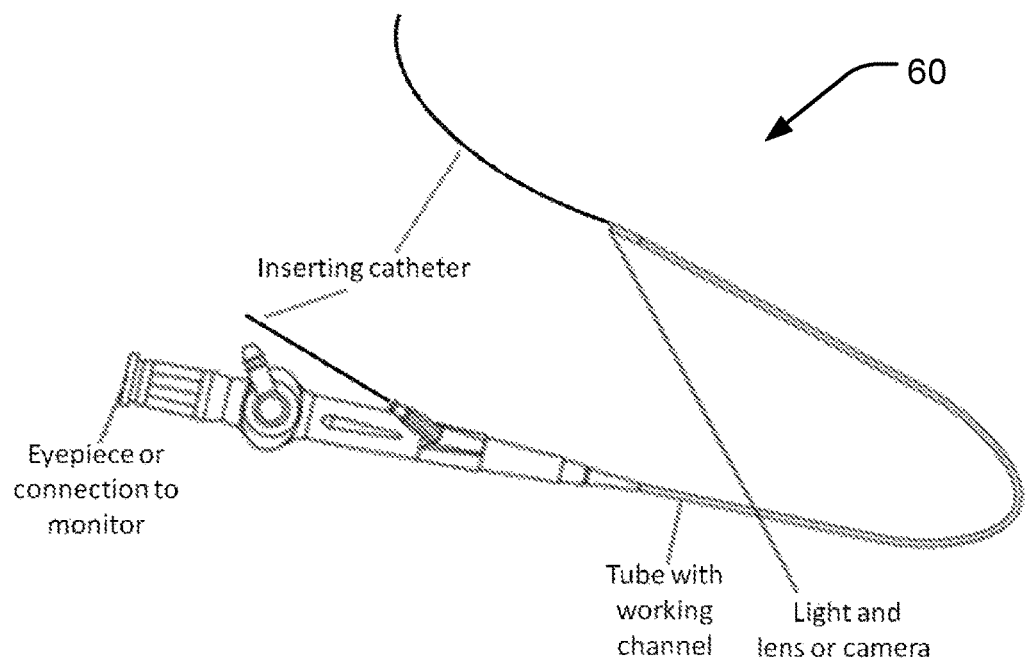
FIG. 12 illustrates an example of an insertion device.
Figure 13:
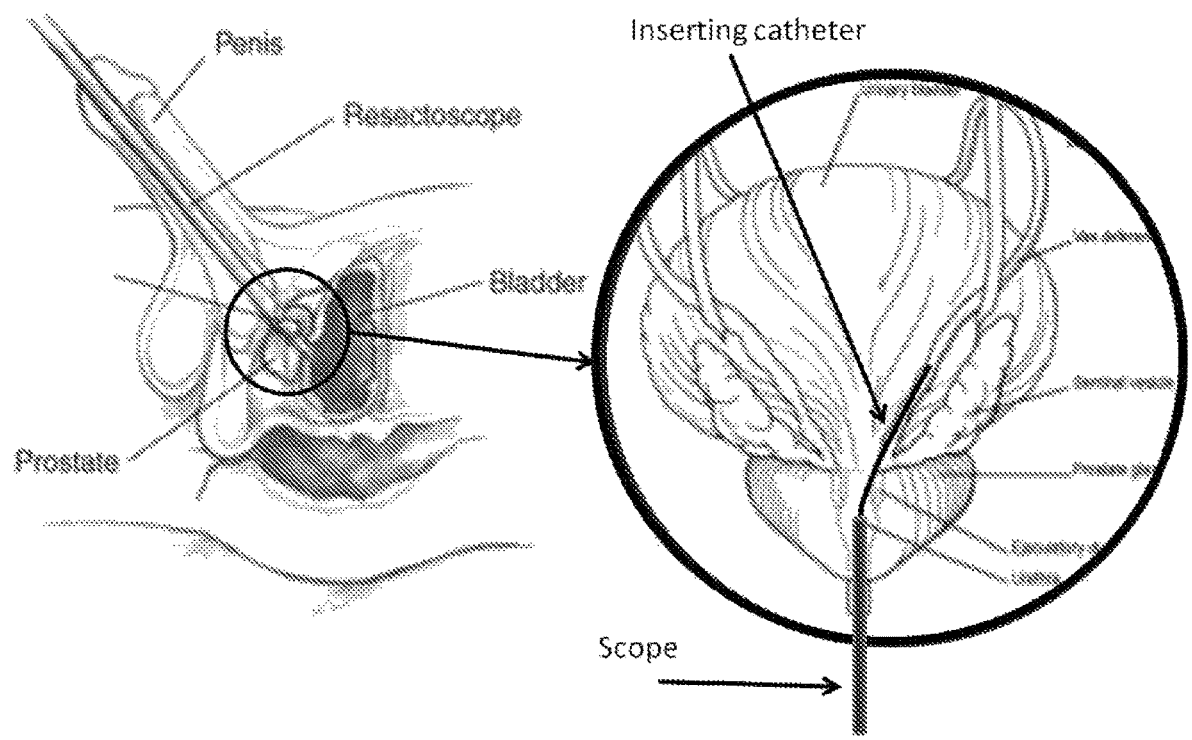
FIG. 13 illustrates the insertion device of FIG. 12 inserted in the mouth of the urethra and guided further into the mouth of the vas deferens through the prostate gland and into the vas deferens.

As already described the occlusion device is inserted into the vas deferens 2 of the male reproductive system, as illustrated in FIG. 2. The insertion of the device is to be explained in the following with reference to FIG. 11.

With the occlusion device according to the invention it is possible to perform a place a plug method without surgery intervention of the vas deferens. The occlusion device 10 is intended to be connected to insertions means fitted to tools (in the below referred to as insertion device 60) used within the same techniques to investigate for example the urinary system and urinary bladder, such as an endoscopic means. The insertion device 60 is thus equipped with a carrying element 65, which in the state of insertion carries the occlusion device 10. By introducing the insertion tool, such as the endoscope or similar into for example the vas deferens of the male gender, the occlusion device is lead into the biological tube, where it is placed approximately in the area 5 of the vas deferens as seen on FIG. 2. Thus, in more detail illustrated in FIG. 11, an insertion device 60 comprises a first end 61 and an opposite second end 62, wherein the first end 61 is configured with a control handle 63 to be operated by a user for insertion of the occlusion device 10 into the biological tube. From the control handle 63 a guiding means 64 extends away from the control handle 63 and towards the second end 62 of the insertion device 60, wherein at this second end 62 the guiding means 64 is provided with a carrying element 65, such as for example a stent, for carrying the occlusion device during guiding of the insertion device within the biological tube. The carrying element has a proximal end 66 adjacent to the guiding means and an opposite distal end. In the proximal end 66 of the carrying element 65, the carrying element 65 is in connection with an end of the guiding means 64, and at the distal end 67 of the carrying device 65 in connection with the occlusion device 10, so that the occlusion device can be placed within the biological tube. Thus the occlusion device is inserted into the biological tube by guiding the occlusion device from the outside into the tube without any surgery method providing damages to the tissue of the biological tube.

In one method, the occlusion device is placed in the vas deferens prior to inflation of the occlusion device to obtain the second volume. With this procedure the occlusion device is inflated after insertion, and afterwards filled with a fluid, for example silicone mixed with a physiological saline solution of 0.9%. In the way, the filling of the occlusion device may be adjusted to the inner diameter of the lumen of the vas deferens, in this way assuring a tight fit within the lumen of the vas deferens. When the patient/male is later interested in restoring the functionality of the vas deferens and thereby the ability to reproduce, the occlusion device is easily removed in the same way it was placed in the biological tube.

Furthermore, with this procedure, the occlusion device could be placed in the vas deferens in a similar manner and with the same techniques used for balloon dilation of blood vessel.

Furthermore in other procedures, the occlusion device could be filled prior to insertion, in which case the occlusion device is pre-fabricated in for example different sizes in order to fit into the lumen of different sized biological tubes.

In one method of inserting the occlusion device into a biological tube, an insertion device with a carrying element, which in the state of insertion releasably carries the occlusion device is inserted into a mouth of a biological tube. The biological tube may be viewed as several biological tubes in series and being in contact with the biological tube, where the occlusion device is to be arranged.

The insertion device is guided though the biological tube(s) until said end reached the desired position of the biological tube, where the occlusion is released from the insertion device and thus arranged at the desired position.

In one type of insertion the insertion device with the occlusion device is inserted in the mouth of the urethra and guided further into the mouth of the vas deferens through the prostate gland and into the vas deferens to the desired location where the occlusion device is arranged.

It is understood that the above method may include other means for inserting the device such as a catheter, which can assist in the insertion process.

It is also apparent that more than one occlusion device may be inserted in different biological tubes, such as inserting an occlusion device in each of the vas deferens tubes leading from each testis.

The device may be removed in the same manner as it was inserted.

The occlusion device may comprise a click lock mechanism, a threading or any other attachment mechanism facilitating removal of the device.

Further a removal device may be used to remove the occlusion device. The removal device may be the same device as the inserting device having instead of the carrying element another removing means arranged on the end that facilitates easy removal of the occlusion device.

The removing means, when inserted into the biological tube, may in one example be able to establish a releasable connection to the removal element of the occlusion device, so that the device is easily removed whilst being connected to the removing means of the removal device.

For testing of the occlusion device and the design thereof, a series of experiments may be designed to make sure that the device is being configured properly in relation to the functionality thereof.

The experiments may be carried out as described in the following, wherein the experiments are divided into three tests:

A test showing that the vas deferens is prone to peristaltic movements under influence from an applied current is performed.

Especially the test may be performed on a spermatic duct taken from pigs. The test preferably showing that the spermatic duct reacts on the applied current by performing peristaltic movements of contraction.

The occlusion device described in this disclosure may be inserted into the spermatic duct of several pigs to test the thesis that the device stays in place within the spermatic duct. That is the device is not pushed out of the spermatic duct due to the peristaltic contractions arising from the applied current. In more detail the current is applied to the spermatic duct, having an occlusion device inserted, by providing two electrodes, which are connected with the muscle tissue. A 5-9VDC is connected to electrodes in order to influence the spermatic duct with electrical impulses.

A test of the change in tissue properties may be performed, to show how the occlusion device after a period of time will stay in place in the spermatic duct. This test may reveal certain requirements to the occlusion device, such as if the design of the occlusion could be changed in dimensions or material in order to more properly stay in place within the spermatic duct of the pigs, eventually within the vas deferens of humans.

The device is inserted into the pigs, by connecting the device to a hypodermic needle together with a physiological saline solution, and thereafter inserting the device into the spermatic duct of a pig, through the use of the hypodermic needle.

Finally, from these described tests, the device may be optimized in shape, dimension and material so find the most proper configuration, which works after the intended function.

In the final test of the occlusion device, having the optimized configuration as defined by the previous described tests, the occlusion device may be inserted into the vas deferens of a pig. The introduction of the occlusion device into the vas deferens may be done by guiding the device through the urinary path of a pig to reach the proper place in the vas deferens. The insertion is done by the use of a stent. Similar test on humans may be performed.

It is to be understood from the present disclosure that the shape of the occlusion device may be altered to accommodate the shape of the biological tube wherein it is to be inserted.

The occlusion device may comprise just one section having an element extending in a radial direction e.g. at least one circumferential flange extending radially and abutting the biological tube when the occlusion device is inserted.

What is claimed is:

1. An occlusion device for blocking a biological tube, said biological tube being prone to a peristaltic wave having a wave length, where said occlusion device comprises:
    at least two sections, each of said at least two sections having a length, lsec, where each of said at least two sections is connected by a narrowing section having a length, lnar, to at least one other section, where a diameter, dnar, of said narrowing section is smaller than the diameter, dsec, of at least one of said at least two sections, wherein said occlusion device is of an elastic material, wherein each of said at least two sections and said narrowing section are configured to contact said biological tube, and each of said at least two sections and said narrowing section are configured to deform independently from other sections and narrowing sections when a force is applied by said peristaltic wave, and the length of at least one of said at least two sections corresponds substantially to the wave length of said peristaltic wave in said biological tube, so as to absorb said peristaltic wave, wherein said biological tube is a vas deferens, and wherein the length of each of said at least two sections is substantially the length of a peristaltic wave arising in the vas deferens, during transportation of spermatozoes through the vas deferens, wherein the occlusion device comprises a first closed end and a second closed end such that the occlusion device is sealed off from the vas deferens, wherein said at least two sections comprise an outer diameter being substantially a size of an inner diameter of said biological tube, an outer diameter of said at least two sections is in a range of approximately 0.1-0.65 mm in diameter, and wherein said narrowing section has a substantially smaller diameter than that of said at least two sections, the diameter of said narrowing section is in a range of 0.05-0.30 mm in diameter.

2. The occlusion device according to claim 1, wherein said at least two sections comprises at least three sections, and said at least three sections are substantially of the same length, lsec.

3. The occlusion device according to claim 1, wherein each of said at least two sections, independently from other sections, is configured to expand and deform under influence from an applied biological pressure, contraction along the length of said occlusion device, or both.

4. The occlusion device according to claim 1, wherein said at least two sections and said narrowing section are configured so that at least one section substantially expands under influence from an applied biological pressure, contraction of said biological tube, or both so that said occlusion device substantially stays in a place of insertion within said biological tube.

5. The occlusion device according to claim 1, wherein said occlusion device is releasable from said biological tube, and is configured to be removed after use without damaging the biological tube.

6. The occlusion device according to claim 1, wherein said at least two sections are of substantially the same length, each of said at least two sections is in a range of approximately 1.5-3.5 mm in length, and said narrowing section in a range of 0.3-0.9 mm in length.

7. The occlusion device according to claim 1, wherein said at least two sections and said narrowing section comprises a hollow interior, which are interconnected so as to allow for passage of a material constrained within a total length of said occlusion device.

8. The occlusion device according to claim 1, wherein said occlusion device is configured to be in a first state having a first volume, and a second state, wherein said occlusion device is expanded to obtain a second larger volume, an expansion is configured to propagate said occlusion device radially, and said second larger volume is obtained by said occlusion device being configured to be inflatable.

9. The occlusion device according to claim 8, wherein the occlusion device is filled with a fluid, gas or a resilient material.

10. The occlusion device according to claim 1, wherein a surface of said occlusion device is provided with a friction-enhancing surface configured to be in contact with an inner wall of said biological tube.

11. The occlusion device according to claim 1, wherein a surface of the occlusion device is treated with a material that is inert to a surface of an inner wall of said biological tube.

12. A method of inserting an occlusion device into a biological tube comprising the steps of:

providing an insertion device with a carrying element, in a state of insertion said carrying element releasably carries the occlusion device, for inserting the occlusion device, inserting and guiding the insertion device through at least one other biological tube before arriving at the biological tube wherein the occlusion device is arranged;

inserting the insertion device into a mouth of the biological tube, guiding the insertion device and the occlusion device into the biological tube, wherein said biological tube is a vas deferens, and wherein the insertion device with the occlusion device is inserted in the mouth of a urethra and guided further into the mouth of the vas deferens through a prostate gland and into the vas deferens to the desired location in the biological tube where the occlusion device is arranged; and arranging the occlusion device at a desired location in the biological tube, wherein said occlusion device comprises at least two sections, wherein each of the at least two sections is connected by a narrowing section, wherein each of said at least two sections and said narrowing section are configured to contact said biological tube, wherein each of said at least two sections and said narrowing section of said occlusion device are configured to deform independently from other sections and narrowing sections when a force is applied by a peristaltic wave, and a length of at least one of said at least two sections of said occlusion device corresponds substantially to a wave length of said peristaltic wave in said biological tube, so as to absorb said peristaltic wave, wherein the occlusion device comprises a first closed end and a second closed end such that the occlusion device is sealed off from the vas deferens, wherein said at least two sections comprise an outer diameter being substantially a size of an inner diameter of said biological tube, an outer diameter of said at least two sections is in a range of approximately 0.1-0.65 mm in diameter, and wherein said narrowing section has a substantially smaller diameter than that of said at least two sections, the diameter of said narrowing section is in a range of 0.05-0.30 mm in diameter.

13. A method of removing an occlusion device from a biological tube comprising the steps of:

providing a removal device with a removing means, which in a state of removal releasably connects with the occlusion device, for removing the occlusion device, inserting and guiding the removal device through at least one other biological tube before arriving at a position of the occlusion device in the biological tube;

inserting the removal device into a mouth of the biological tube, guiding the removal device into the biological tube until it reaches the occlusion device, wherein said biological tube is a vas deferens, and wherein the removal device with the removing means is inserted in the mouth of a urethra and guided further into the mouth of the vas deferens located in a prostate gland and into the vas deferens to a location of the occlusion device, wherein said occlusion device comprises at least two sections, wherein each of the at least two sections is connected by a narrowing section, wherein each of said at least two sections and said narrowing section are configured to contact said biological tube, wherein each of said at least two sections and said narrowing section of said occlusion device are configured to deform independently from other sections and narrowing sections when a force is applied by a peristaltic wave, and a length of at least one of said at least two sections of said occlusion device corresponds substantially to a wave length of said peristaltic wave in said biological tube, so as to absorb said peristaltic wave, wherein the occlusion device comprises a first closed end and a second closed end such that the occlusion device is sealed off from the vas deferens, wherein said at least two sections comprise an outer diameter being substantially a size of an inner diameter of said biological tube, an outer diameter of said at least two sections is in a range of approximately 0.1-0.65 mm in diameter, and wherein said narrowing section has a substantially smaller diameter than that of said at least two sections, the diameter of said narrowing section is in a range of 0.05-0.30 mm in diameter; and establishing a releasable connection between the removing means and the occlusion device, so that the occlusion device can be removed from the biological tube by guiding it out through said biological tube.

* * * * *